(12) United States Patent
Xu et al.

(10) Patent No.: US 12,145,910 B2
(45) Date of Patent: Nov. 19, 2024

(54) METHOD FOR SYNTHESIZING 3-SPIRO THREE-MEMBERED RING INDOLINONE DERIVATIVE

(71) Applicant: SOOCHOW UNIVERSITY, Suzhou (CN)

(72) Inventors: Xiaoping Xu, Suzhou (CN); Shunjun Ji, Suzhou (CN); Ruiying Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 598 days.

(21) Appl. No.: 17/613,472

(22) PCT Filed: Oct. 26, 2020

(86) PCT No.: PCT/CN2020/123620
§ 371 (c)(1),
(2) Date: Nov. 22, 2021

(87) PCT Pub. No.: WO2022/082817
PCT Pub. Date: Apr. 28, 2022

(65) Prior Publication Data
US 2022/0315533 A1    Oct. 6, 2022

(30) Foreign Application Priority Data
Oct. 20, 2020  (CN) .......................... 202011125496.7

(51) Int. Cl.
C07D 209/96    (2006.01)
(52) U.S. Cl.
CPC .................. C07D 209/96 (2013.01)
(58) Field of Classification Search
CPC .................................................. C07D 209/96
See application file for complete search history.

(56) References Cited

FOREIGN PATENT DOCUMENTS

| CN | 108276324 A | 7/2018 |
|---|---|---|
| CN | 109608456 A | 4/2019 |
| WO | 2010115279 A1 | 10/2010 |
| WO | 2011123947 A1 | 10/2011 |

OTHER PUBLICATIONS

Moriconi et al., Journal of Organic Chemistry (1964), 29(12), pp. 3577-3584. (Year: 1964).*
Cao et al., Highly Stereoselective OleIn Cyclopropanation of Diazooxindoles Catalyzed by a C2!Symmetric Spiroketal Bisphosphine/Au(I) Complex, Journal of the American Chemical Society, 2013, 135, 8197-8200 (May 22, 2013).
Ladd et al., Silver-Promoted, Palladium-Catalyzed Direct Arylation of Cyclopropanes: Facile Access to Spiro 3,30- Cyclopropyl Oxindoles, Organic Letters, 2013, vol. 15, No. 6, 1350-1353 (Mar. 1, 2013).

* cited by examiner

*Primary Examiner* — Laura L Stockton
(74) *Attorney, Agent, or Firm* — SZDC Law PC

(57) ABSTRACT

The present invention provides a method for synthesizing a 3-spiro three-membered ring indolinone derivative, which comprises under a protective atmosphere, reacting a 3-indolethanol compound as a reaction raw material at 20-60° C. in the presence of an additive and an organic base in an organic solvent, to obtain a 3-spiro three-membered ring indolinone compound after the reaction is complete. The additive is N-bromosuccinimide (NBS) or N-chlorosuccinimide (NCS). The method of the present invention does not require a metal catalyst, and the 3-spiro three-membered ring indolinone derivative is synthesized in one step in the presence of NBS or NCS. The reaction conditions are mild, the operations are simple and safe, and the yield is high.

10 Claims, No Drawings

METHOD FOR SYNTHESIZING 3-SPIRO THREE-MEMBERED RING INDOLINONE DERIVATIVE

This application is the National Stage Application of PCT/CN2020/123620, filed on Oct. 26, 2020, which claims priority to Chinese Patent Application No. 202011125496.7, filed on Oct. 20, 2020.

FIELD OF THE INVENTION

The present invention relates to the technical field of organic synthesis, and more particularly to a method for synthesizing a 3-spiro three-membered ring indolinone derivative.

DESCRIPTION OF THE RELATED ART

Spiro(3,3'-cyclopropane)-2-indolinone, which integrates two important pharmacodynamic groups, 2-indolinone and cyclopropane skeleton, has attracted much attention in the field of drug development and synthetic chemistry research. Such spiro skeletons can be found in a variety of pesticides and pharmaceutical molecules, including anti-HIV drugs, obesity inhibitors, adrenaline agonists, and anti-respiratory syncytial virus compounds. In addition, Carreira et al. also proved that spiro[3,3'-cyclopropane]indolinone is a multifunctional synthon (*Angew. Chem., Int. Ed.* 1999, 111, 3379-3381, *J. Am. Chem. Soc.* 2005, 127, 11505-11515, *J. Am. Chem. Soc.* 2002, 124, 14826-14827), and the spiro [pyrrolidine-3,3'-indol] ring can be synthesized by the ring expansion reaction of imine to prepare a variety of alkaloids present in natural products.

At present, the methods for synthesizing spiro(3,3'-cyclopropane)-2-indolinone has some drawbacks as follows: 1) The alkyl chain needs to be introduced into the substrate before the cyclization reaction is carried out. This two-step synthesis method largely inhibits the efficient synthesis of such compounds. 2) The reaction substrate involves dangerous reagents, such as diazonium compounds. 3) It is necessary to use salts of precious metals such as palladium and silver, which is not economical and requires high cost.

SUMMARY OF THE INVENTION

In order to solve the above technical problems, an object of the present invention is to provide a method for synthesizing a 3-spiro three-membered ring indolinone derivative. The method of the present invention does not require the use of a metal catalyst, and the 3-spiro three-membered ring indolinone derivative is synthesized in one step in the presence of NBS or NCS. The reaction conditions are mild, the operations are simple and safe, and the yield is high.

The object of the present invention is to provide a method for synthesizing a 3-spiro three-membered ring indolinone derivative, including the following steps:

under a protective atmosphere, a compound of formula (I) or formula (III) reacts at 20-60° C. in the presence of an additive and an organic base in an organic solvent, to obtain a compound of formula (II) or formula (IV) after the reaction is complete, where the additive is selected from N-bromosuccinimide (NBS) or N-chlorosuccinimide (NCS); and the reaction routes are respectively as follows, where formula (I) is other than formula (III):

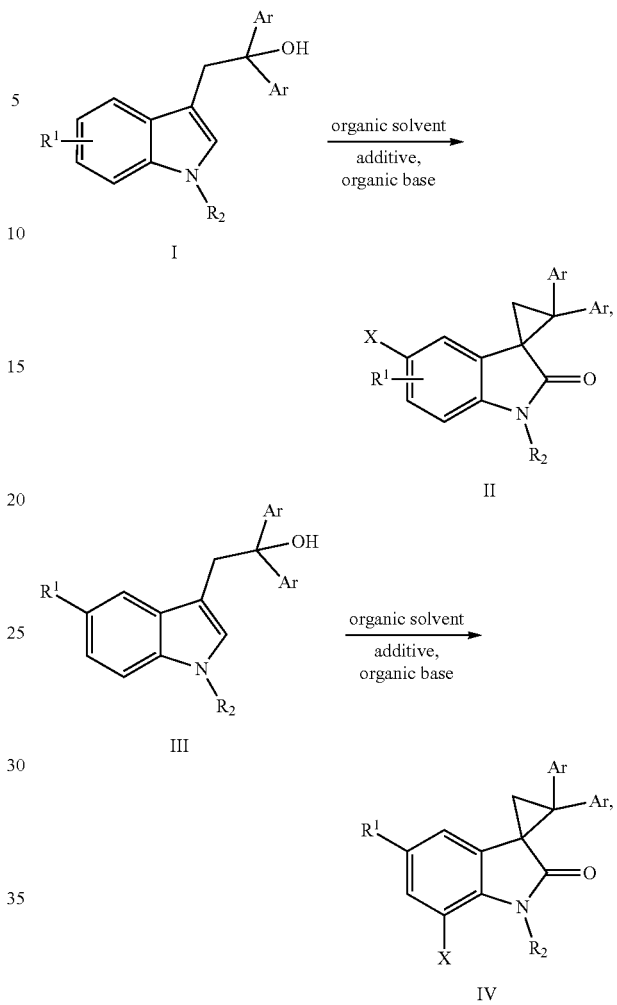

where in formulas (I)-(IV), $R^1$ is hydrogen, C1-C4 alkyl or halo; R2 is selected from hydrogen, C1-C4 alkyl, benzyl or phenyl; Ar is selected from phenyl, substituted phenyl or thienyl, the substituent on the substituted phenyl is selected from the group consisting of halo, C1-C4 alkyl, C1-C4 alkoxy or any combination; and X is selected from chloro or bromo.

Preferably, the organic base is selected from the group consisting of triethylenediamine (DABCO), 1,8-diazabicycloundec-7-ene (DBU), sodium hydride (NaH), triethylamine ($Et_3N$) and any combination thereof. More preferably, the organic base is selected from $Et_3N$.

Preferably, the molar ratio of the compound of formula (I) or formula (III) to the additive is 1:1-3, and more preferably 1:2.

Preferably, the organic solvent is selected from the group consisting of 1,2-dichloroethane, 1,2-dichloromethane, toluene, 1,4-dioxane, ethyl acetate, acetonitrile and any combination thereof. More preferably, the organic solvent is acetonitrile ($CH_3CN$).

Preferably, $R^1$ is selected from hydrogen, methyl or halo.

Preferably, $R^2$ is selected from hydrogen, methyl, benzyl or phenyl.

Preferably, Ar is selected from phenyl, substituted phenyl or thienyl, in which the substituent on the substituted phenyl is selected from halo, methoxy or methyl.

Preferably, the reaction time is 6-15 h. More preferably, the reaction time is 8 h.

Preferably, the protective atmosphere is selected from argon (Ar), oxygen (O₂), air and any combination thereof.

Preferably, the halo is selected from fluoro, chloro or bromo.

Preferably, the additive is NBS. The reaction temperature is preferably 25° C.

Preferably, the compound of formula (I) or formula (III) is selected from 2-(1-methyl-1H-indol-3-yl)-1,1-diphenylethan-1-ol (1), 1,1-bis(4-fluorophenyl)-2-(1-methyl-1H-indol-3-yl)ethan-1-ol (2), 1,1-bis(4-methoxyphenyl)-2-(1-methyl-1H-indol-3-yl)ethan-1-ol (3), 2-(1-methyl-1H-indol-3-yl)-1,1-di-p-tolyl-1-ol (4), 2-(1-methyl-1H-indol-3-yl)-1,1-bis(thiophen-2-yl)ethan-1-ol (5), 1,1-diphenyl-2-(1-phenyl-1H-indol-3-yl)ethan-1-ol (6), 1,1-bis(4-fluorophenyl)-2-(1-phenyl-1H-indol-3-yl)ethan-1-ol (7), 2-(1-phenyl-1H-indol-3-yl)-1,1-di-p-tolyl-1-ol (8), 2-(1-benzyl-1H-indol-3-yl)-1,1-diphenylethan-1-ol (9), 2-(1H-indol-3-yl)-1,1-diphenylethan-1-ol (10), 1,1-bis(3-fluorophenyl)-2-(1H-indol-3-yl)ethan-1-ol (11), 2-(1H-indol-3-yl)-1,1-di-m-tolyl-1-ol (12), 1,1-bis(4-fluorophenyl)-2-(1H-indol-3-yl)ethan-1-ol (13), 2-(1H-indol-3-yl)-1,1-di-p-tolyl-1-ol (14), 2-(6-chloro-1H-indol-3-yl)-1,1-diphenylethan-1-ol (15), 2-(6-bromo-1H-indol-3-yl)-1,1-diphenylethan-1-ol (16), 2-(6-methyl-1H-indol-3-yl)-1,1-diphenylethan-1-ol (17), 2-(7-methyl-1H-indol-3-yl)-1,1-diphenylethan-1-ol (18), 2-(5-fluoro-1H-indol-3-yl)-1,1-diphenylethan-1-ol (19), 2-(5-chloro-1H-indol-3-yl)-1,1-diphenylethan-1-ol (20), or 2-(5-bromo-1H-indol-3-yl)-1,1-diphenylethan-1-ol (21). The specific structural formulas corresponding to the above serial numbers are as follows:

(1)
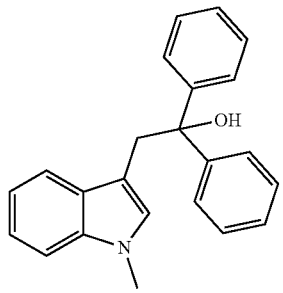

(2)
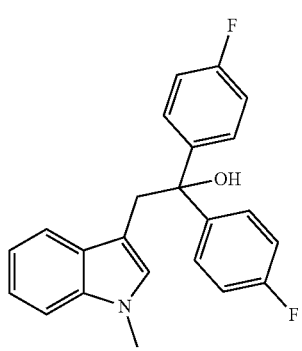

-continued (3)
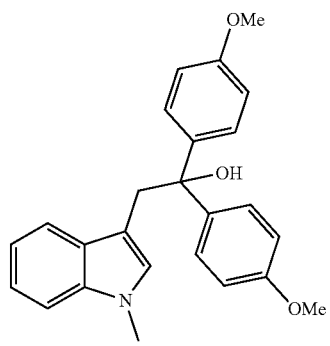

(4)
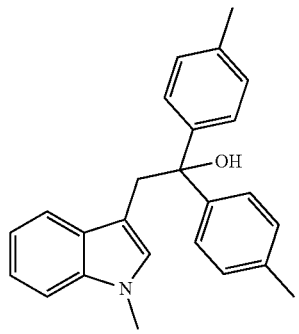

(5)
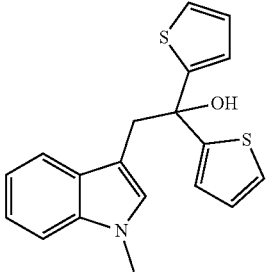

(6)
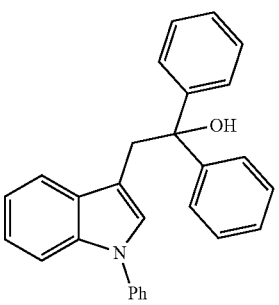

(7)
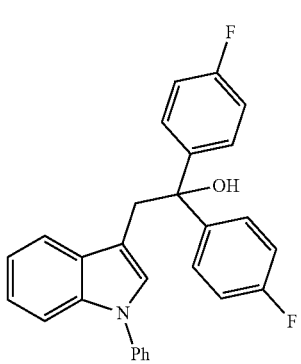

(8)
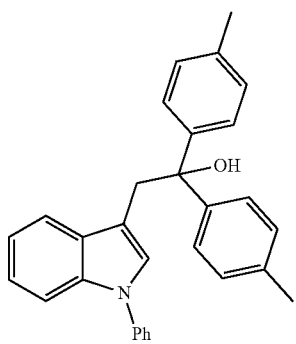
(9)
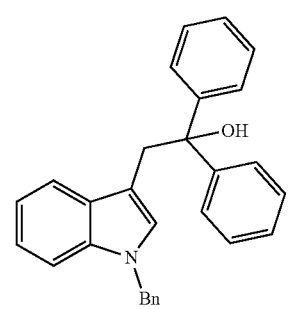
(10)
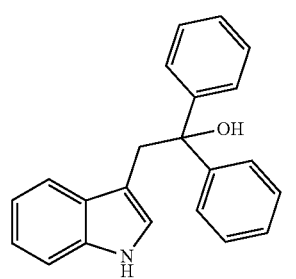
(11)
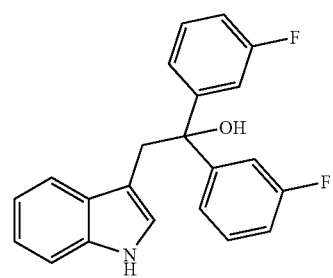
(12)
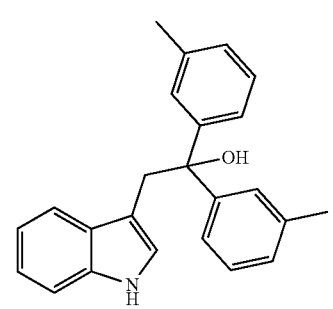
(13)
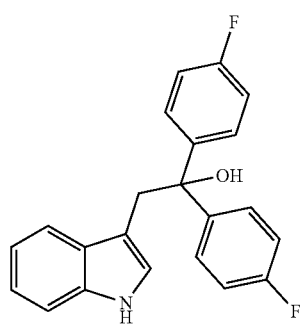
(14)
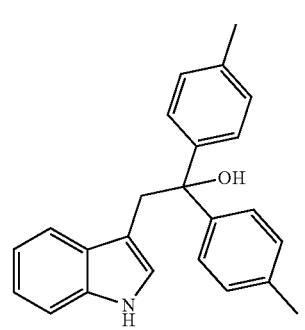
(15)
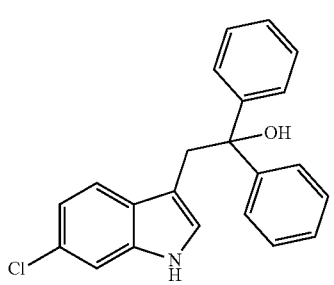
(16)
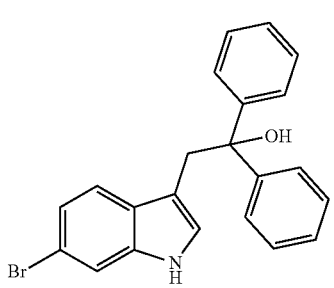
(17)
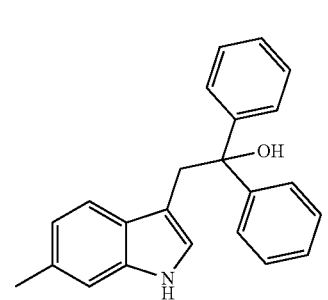

(18)

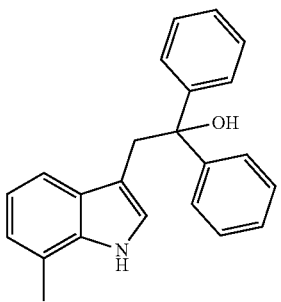

(19)

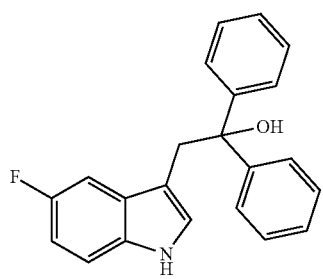

(20)

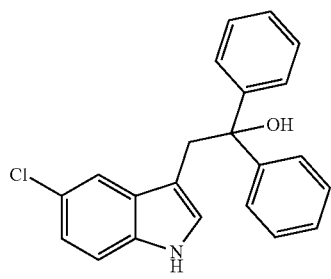

(21)

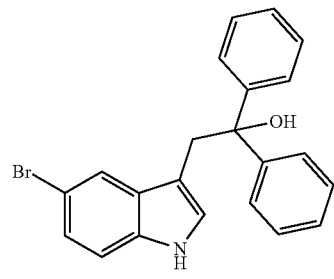

Preferably, the compound of formula (II) or formula (IV) is selected from 5'-bromo-1'-methyl-2,2-diphenylspiro[cyclopropane-1,3'-indol]-2'-ketone (22), 5'-bromo-2,2-bis(4-fluorophenyl)-1'-methyl spiro[cyclopropane-1,3'-indol]-2'-one (23), 5'-bromo-2,2-bis(4-methoxyphenyl)-1'-methyl spiro[cyclopropane-1,3'-indol]-2'-one (24), 5'-bromo-1'-methyl-2,2-di-p-tolylspiro[cyclopropane-1,3'-indol]-2'-one (25), 5'-bromo-1'-methyl-2-(thiophen-2-yl)-2-(thiophen-3-yl)spiro[cyclopropane-1,3'-indol]-2'-one (26), 1',2,2-triphenylspiro[cyclopropane-1,3'-indol]-2'-one (27), 2,2-bis(4-fluorophenyl)-1'-phenylspiro[cyclopropane-1,3'-indol]-2'-one (28), 1'-phenyl-2,2-di-p-tolylspiro[cyclopropane-1,3'-indol]-2'-one (29), 1'-benzyl-5'-bromo-2,2-diphenylspiro[cyclopropane-1,3'-indol]-2'-one (30), 5'-chloro-1'-methyl-2,2-diphenylspiro[cyclopropane-1,3'-indol]-2'-one (31), 5'-bromo-2,2-diphenylspiro[cyclopropane-1,3'-indol]-2'-one (32), 5'-bromo-2,2-bis(4-fluorophenyl)spiro[cyclopropane-1,3'-indol]-2'-one (33), 5'-bromo-2,2-di-p-tolylspiro[cyclopropane-1,3'-indol]-2'-one (34), 5'-bromo-2,2-bis(3-fluorophenyl)spiro[cyclopropane-1,3'-indol]-2'-one (35), 5'-bromo-2,2-di-m-tolylspiro[cyclopropane-1,3'-indol]-2'-one (36), 5'-bromo-6'-chloro-2,2-diphenylspiro[cyclopropane-1,3'-indol]-2'-one (37), 5',6'-dibromo-2,2-diphenylspiro[cyclopropane-1,3'-indol]-2'-one (38), 5'-bromo-6'-methyl-2,2-diphenylspiro[cyclopropane-1,3'-indol]-2'-one (39), 5'-bromo-7'-methyl-2,2-diphenylspiro[cyclopropane-1,3'-indol]-2'-one (40), 7'-bromo-5'-fluoro-2,2-diphenylspiro[cyclopropane-1,3'-indol]-2'-one (41), 7'-bromo-5'-chloro-2,2-diphenylspiro[cyclopropane-1,3'-indol]-2'-one (42), or or 5',7'-dibromo-1'-methyl-2,2-diphenylspiro[cyclopropane-1,3'-indol]-2'-one (43). The specific structural formulas corresponding to the above serial numbers are as follows:

22

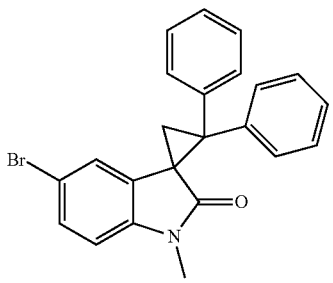

23

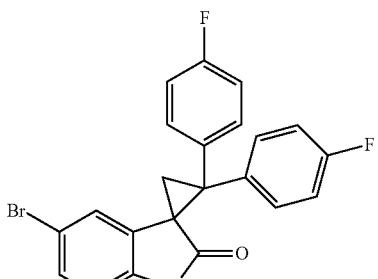

24

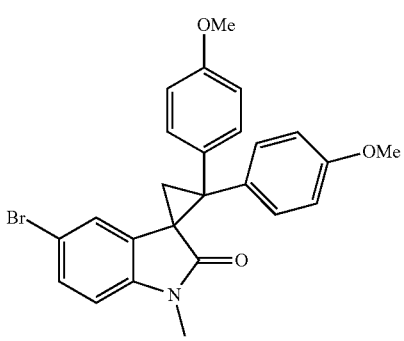

25

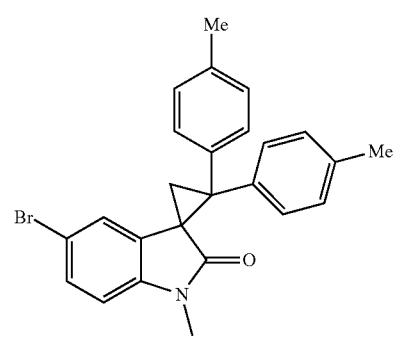

| | |
|---|---|
| 26 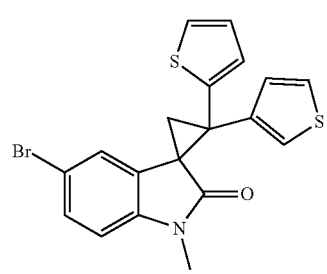 | 31 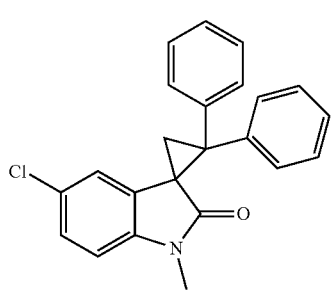 |
| 27 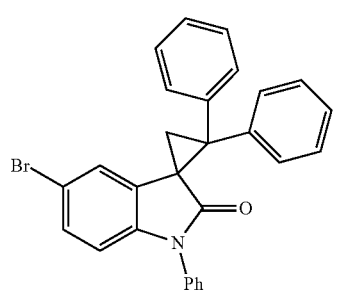 | 32 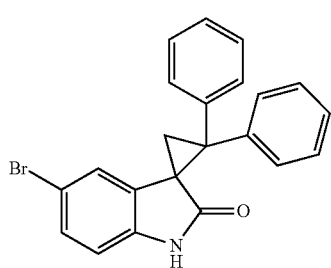 |
| 28 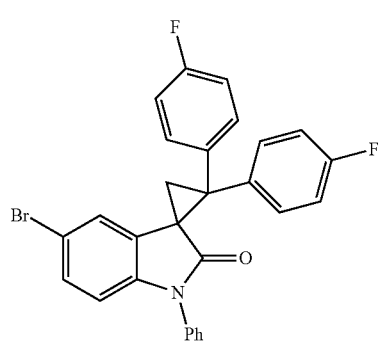 | 33 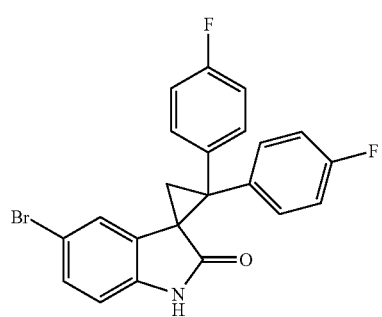 |
| 29 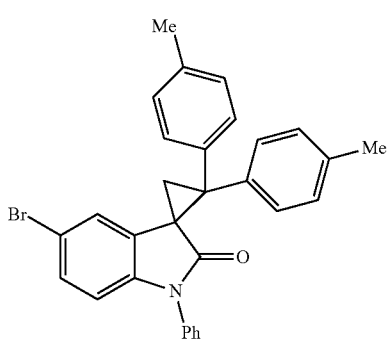 | 34 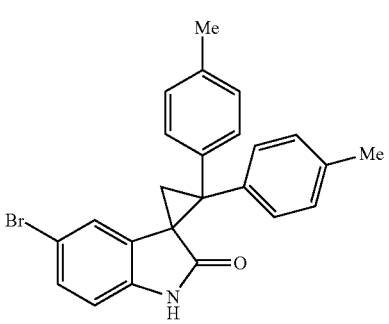 |
| 30 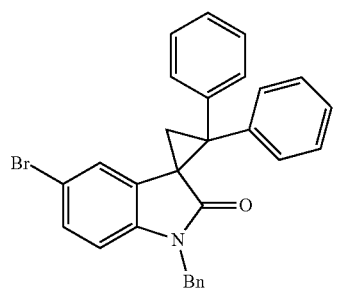 | 35 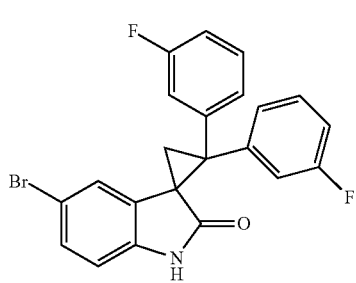 |

36

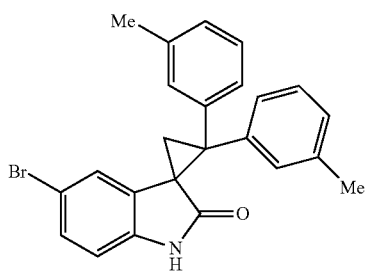

37

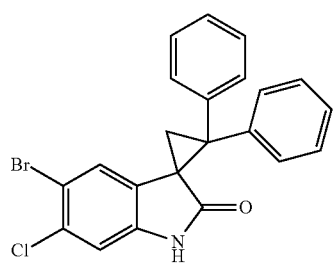

38

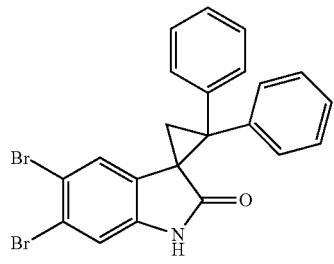

39

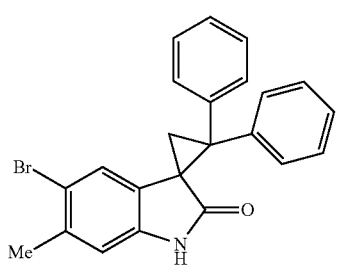

41

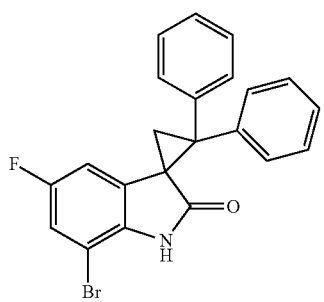

42

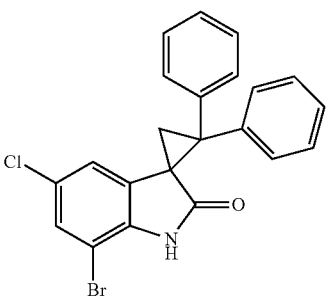

43

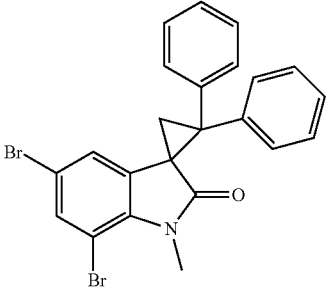

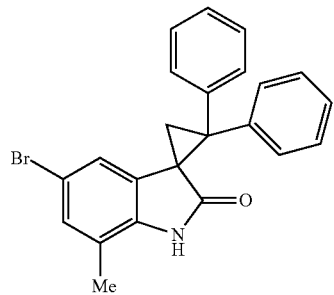

Preferably, the above synthesis method also includes a step of purifying the compound of formula (II) or formula (IV) by column chromatography after the reaction is complete.

Taking the reaction involving 2-(1H-indol-3-yl)-1,1-diphenylethan-1-ol and N-bromosuccinimide (NBS) as an example, the reaction principle of the present invention is described as follows:

Because formula (I) is exclusive of formula (III), i.e., the compound of formula (I) has no substituent at C(5), a bromium ion intermediate A is formed in the presence of NBS. Then the alcoholic hydroxyl group on a side chain attached to indole nucleophilically attacks the position 2 of indole, which causes ring closing. At the same time, the benzene ring in indole receives the electrophilic substitution of Br⁺ in the system to obtain an intermediate B. In an alkaline environment, one molecule of HBr is removed from the intermediate B, to obtain an aromatized intermediate C. Due to the existence of two phenyl groups, the indolinofuran skeleton of the intermediate C is unstable in the system, and the C—O bond breaks very easily to realize the migration of oxygen atoms, so the intermediate C is finally converted into a stable spiro three-membered ring indolinone product of formula II.

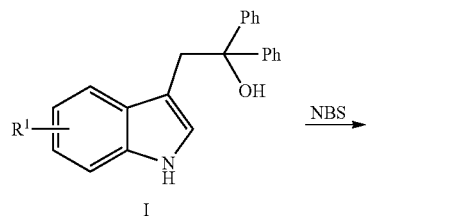

I

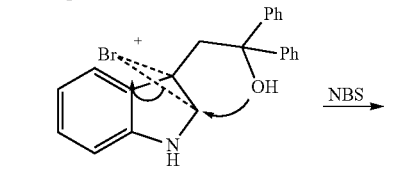

A

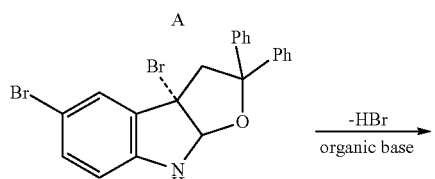

B

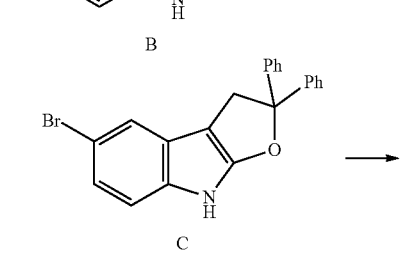

C

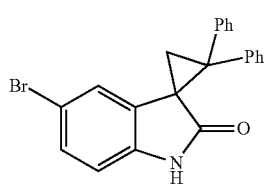

II

When C(5) is substituted, i.e., when the compound of formula (III) is used as the raw material, it undergoes a reaction process similar to the above process. However, during the reaction, because C(5) is substituted, when the benzene ring in indole receives the electrophilic substitution of Br+ in the system, the electrophilic substitution occurs at the C(7) position to obtain an intermediate E, and then finally obtain the 7-bromo target product of formula IV:

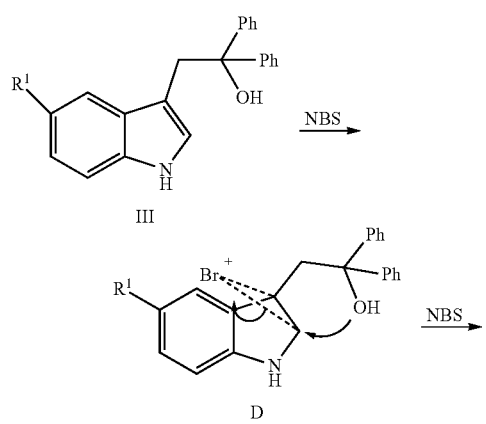

-continued

[Structure E]

[Structure F]

[Structure IV]

In the present invention, a 3-indol-ethanol compound is used as a reaction material, and in the presence of the additive NBS or NCS in an alkaline environment of an organic base, a 3-spiro three-membered ring indolinone compound is prepared by one-pot method. By means of the above solutions, the present invention has the following advantages.

(1) The preparation of spiroindolinone containing two important pharmacodynamic groups, 2-indolinone and cyclopropane skeleton, is achieved by using one-pot method, which is more economical and efficient than the conventional method that requires substrate pre-functionalization before cyclization.

(2) The molecular core skeleton of the 3-spiro three-membered ring indolinone derivative of the present invention can be used to synthesize a spiro[pyrrolidine-3,3'-indol] ring by a ring expansion reaction, which can then be used to prepare a variety of alkaloids that are present in natural products. Thus, the potential application value of such compounds in biological activity is improved.

(3) The product of the present invention, the 3-spiro three-membered ring indolinone derivative, has successfully achieved a gram-level reaction scale with a good yield, which provides a good basis for the mass production and wide application of such compounds in the future.

(4) The present invention provides a safer, more economical and efficient synthesis method.

The above description is only a summary of the technical solutions of the present invention. To make the technical means of the present invention clearer and implementable in accordance with the disclosure of the specification, the preferred embodiments of the present invention will be described in detail with reference to the accompanying drawings.

DETAILED DESCRIPTION OF THE PREFERRED EMBODIMENTS

The specific embodiments of the present invention will be described in further detail with reference to examples. The following examples are intended to illustrate the present invention, instead of limiting the scope of the present invention.

In the present invention, the specific structural formulas of NBS, NCS and NIS involved are as follows, and the compounds corresponding to other serial numbers are the same as those in the description above:

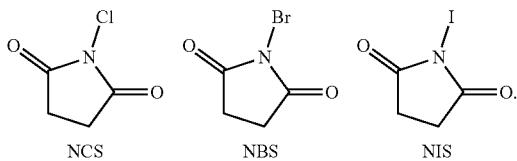

Example 1

Synthesis of 5'-bromo-1'-methyl-2,2-diphenylspiro[cyclopropane-1,3'-indol]-2'-one (22)

2-(1-methyl-1H-indol-3-yl)-1,1-diphenylethan-1-ol (Compound No. (1), 0.2 mmol, 0.0654 g) and NBS (0.4 mmol, 0.0712 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0669 g).

The above reaction product was characterized: $^1$H NMR (400 MHz, Chloroform-d) δ=7.29 (d, J=8.0 Hz, 2H), 7.22-7.20 (m, 2H), 7.19-7.16 (m, 6H), 7.11 (t, J=8.0 Hz, 1H), 6.66 (d, J=8.0 Hz, 1H), 5.59 (s, 1H), 3.15 (s, 3H), 2.58 (d, J=4.0 Hz, 1H), 2.29 (d, J=4.0 Hz, 1H) ppm. According to the characterization data, the obtained reaction product is pure 5'-bromo-1'-methyl-2,2-diphenylspiro[cyclopropane-1,3'-indol]-2'-one (purity>95%). The product yield is calculated to be 83%.

Example 2

Synthesis of 1',2,2-triphenylspiro[cyclopropane-1,3'-indol]-2'-one (27)

1,1-diphenyl-2-(1-phenyl-1H-indol-3-yl)ethan-1-ol (Compound No. (6), 0.2 mmol, 0.0778 g) and NBS (0.4 mmol, 0.0712 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0519 g).

The above reaction product was characterized: $^1$H NMR (400 MHz, Chloroform-d) δ=7.56-7.44 (m, 6H), 7.43-7.35 (m, 3H), 7.32-7.26 (m, 5H), 7.20 (d, J=8.0 Hz, 1H), 7.14 (d, J=8.0 Hz, 1H), 6.97 (d, J=8.0 Hz, 1H), 6.74 (t, J=8.0 Hz, 1H), 5.76 (d, J=8.0 Hz, 1H), 2.80 (d, J=4.0 Hz, 1H), 2.50 (d, J=4.0 Hz, 1H) ppm. According to the characterization data, the obtained reaction product is pure 1',2,2-triphenylspiro[cyclopropane-1,3'-indol]-2'-one (purity>95%). The product yield is calculated to be 66%.

Example 3

Synthesis of 1'-benzyl-5'-bromo-2,2-diphenylspiro[cyclopropane-1,3'-indol]-2'-one (30)

2-(1-benzyl-1H-indol-3-yl)-1,1-diphenylethan-1-ol (Compound No. (9), 0.2 mmol, 0.0806 g) and NBS (0.4 mmol, 0.0712 g) were weighed and added to a 25 mL reaction tube, and purged for three times. Acetonitrile (2 mL) was added as a solvent, and finally triethylamine (55.8 μL) was added. The mixture was stirred reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0692 g).

The above reaction product was characterized: $^1$H NMR (400 MHz, Chloroform-d) δ=7.41 (d, J=8.0 Hz, 2H), 7.39-7.32 (m, 5H), 7.32-7.30 (m, 2H), 7.29 (d, J=4.0 Hz, 5H), 7.25 (d, J=8.0 Hz, 1H), 7.21 (dd, J=8.0, 2.0 Hz, 1H), 6.70 (d, J=8.0 Hz, 1H), 5.71 (d, J=2.0 Hz, 1H), 5.05 (d, J=16.0 Hz, 1H), 4.85 (d, J=16.0 Hz, 1H), 2.78 (d, J=4.0 Hz, 1H), 2.45 (d, J=4.0 Hz, 1H) ppm. According to the characterization data, the obtained reaction product is pure 1'-benzyl-5'-bromo-2,2-diphenylspiro[cyclopropane-1,3'-indol]-2'-one (purity>95%). The product yield is calculated to be 72%.

Example 4

Synthesis of 5'-chloro-1'-methyl-2,2-diphenylspiro[cyclopropane-1,3'-indol]-2'-one (31)

2-(1-methyl-1H-indol-3-yl)-1,1-diphenylethan-1-ol (Compound No. (1), 0.2 mmol, 0.0654 g) and NCS (0.4 mmol, 0.0532 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0421 g).

The above reaction product was characterized: $^1$H NMR (400 MHz, Chloroform-d) δ=7.38 (d, J=8.0 Hz, 2H), 7.28-7.24 (m, 4H), 7.23 (s, 1H), 7.21-7.20 m, 2H), 7.18 (s, 1H), 6.88 (d, J=8.0 Hz, 1H), 6.67 (t, J=8.0 Hz, 1H), 5.64 (d, J=8.0 Hz, 1H), 3.26 (s, 3H), 2.64 (d, J=4.0 Hz, 1H), 2.36 (d, J=4.0 Hz, 1H) ppm. According to the characterization data, the obtained reaction product is pure 5'-chloro-1'-methyl-2,2- diphenylspiro[cyclopropane-1,3'-indol]-2'-one (purity>95%). The product yield is calculated to be 58%.

Example 5

Synthesis of 5'-bromo-2,2-diphenylspiro[cyclopropane-1,3'-indol]-2'-one (32)

2-(1H-indol-3-yl)-1,1-diphenylethan-1-ol (Compound No. (10), 0.2 mmol, 0.0626 g) and NBS (0.4 mmol, 0.0712 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0601 g).

The above reaction product was characterized: $^1$H NMR (400 MHz, Chloroform-d) δ=9.08 (s, 1H), 7.40 (d, J=8.0 Hz, 2H), 7.28-7.24 (m, 7H), 7.19 (t, J=8.0 Hz, 2H), 6.55 (d, J=8.0 Hz, 1H), 5.63 (s, 1H), 2.65 (d, J=4.0 Hz, 1H), 2.40 (d, J=4.0 Hz, 1H) ppm. According to the characterization data, the obtained reaction product is pure 5'-bromo-2,2-diphenylspiro[cyclopropane-1,3'-indol]-2'-one (purity>95%). The product yield is calculated to be 77%.

Example 6

Synthesis of 5',7'-dibromo-1'-methyl-2,2-diphenylspiro[cyclopropane-1,3'-indol]-2'-one (43)

2-(5-bromo-1H-indol-3-yl)-1,1-diphenylethan-1-ol (Compound No. (21), 0.2 mmol, 0.0506 g) and NBS (0.4 mmol, 0.0712 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6), to obtain the reaction product (0.0698 g).

The above reaction product was characterized: $^1$H NMR (400 MHz, DMSO-d6) δ=11.01 (s, 1H), 7.50 (s, 1H), 7.43 (d, J=8.0 Hz, 2H), 7.35 (s, 2H), 7.31-7.21 (m, 5H), 7.17 (d, J=8.0 Hz, 1H), 5.54 (s, 1H), 2.64 (d, J=4.0 Hz, 1H), 2.43 (d, J=4.0 Hz, 1H) ppm. According to the characterization data, the obtained reaction product is pure 5',7'-dibromo-1'-methyl-2,2-diphenylspiro[cyclopropane-1,3'-indol]-2'-one (purity>95%). The product yield is calculated to be 73%.

Comparative Example 1

2-(1-methyl-1H-indol-3-yl)-1,1-diphenylethan-1-ol (Compound No. (1), 0.2 mmol, 0.0654 g) and NIS (0.4 mmol, 0.0900 g) were weighed and added to a 25 mL reaction tube, and purged for three times. Acetonitrile (2 mL) was added as a solvent, and finally triethylamine (55.8 μL) was added. The mixture was reacted at room temperature for 8 h under stirring. After the reaction was complete, the reaction solution was concentrated under vacuum and then separated by column chromatography (stationary phase: 200-300 mesh silica gel powder, mobile phases: ethyl acetate (A) and petroleum ether (B), and change program (A:B) of mobile phases: 1:6). The target product was not obtained through separation, indicating a low yield of the product when NIS is used as the additive.

In conclusion, the present invention provides a reaction model based on the 3-indole ethanol and one-pot method, which involves a high-efficiency cascade process such as dearomatization, five-membered cyclization/dehydrohalogenation aromatization/intramolecular oxygen migration and synergistic ring condensation, to construct a series of spirocyclic indolinone derivatives with potential biological activity. The reaction raw materials are simple and readily available, the conditions are mild, the use of metal catalysts is avoided, the substrate has good generality and excellent atom economy. The molecular core skeleton of the product can be used to synthesize a spiro[pyrrolidine-3,3'-indol] ring by a ring expansion reaction, which can then be used to prepare a variety of alkaloids existing in natural products. Thus, the potential application value of such compounds in biological activity is improved.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for synthesizing a 3-spiro three-membered ring indolinone derivative, comprising steps of:

under a protective atmosphere, reacting a compound of formula (I) or formula (III) at 20-60° C. in the presence of an additive and an organic base in an organic solvent, to obtain a compound of formula (II) or formula (IV) after the reaction is complete, wherein the additive is N-bromosuccinimide (NBS) or N-chlorosuccinimide (NCS); and the reaction routes are as follows, wherein the formula (I) is exclusive of the formula (III):

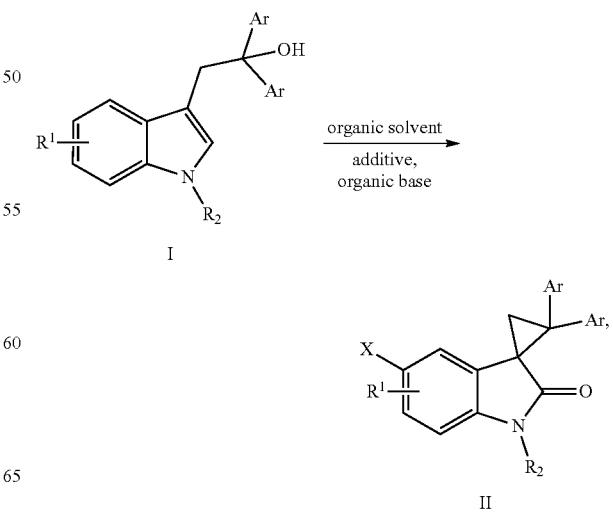

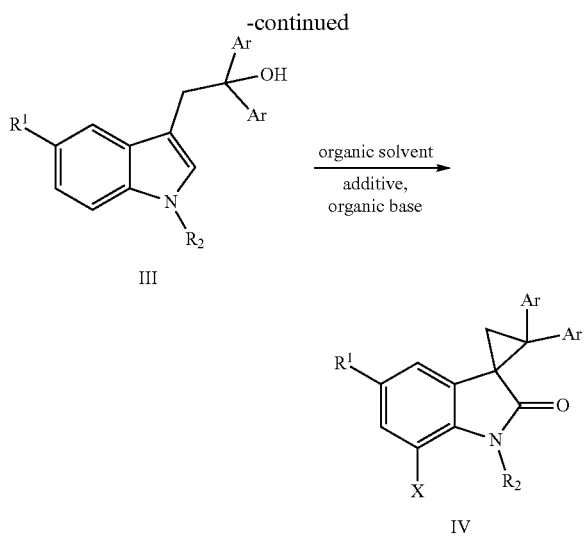

wherein in formulas (I)-(IV), $R^1$ is selected from hydrogen, C1-C4 alkyl or halo; $R^2$ is hydrogen, C1-C4 alkyl, benzyl or phenyl; Ar is selected from phenyl, substituted phenyl or thienyl, in which the substituent on the substituted phenyl is selected from the group consisting of halo, C1-C4 alkyl, C1-C4 alkoxy or any combination thereof; and X is chloro or bromo.

2. The method according to claim 1, wherein the organic base is selected from the group consisting of triethylenediamine, 1,8-diazabicycloundec-7-ene, sodium hydride, trimethylamine and any combination thereof.

3. The method according to claim 1, wherein the molar ratio of the compound of formula (I) or formula (III) to the additive is 1:1-3.

4. The method according to claim 1, wherein the organic solvent is selected from the group consisting of 1,2-dichloroethane, 1,2-dichloromethane, toluene, 1,4-dioxane, ethyl acetate, acetonitrile and any combination thereof.

5. The method according to claim 1, wherein R1 is selected from hydrogen, methyl or halo.

6. The method according to claim 1, wherein R2 is selected from hydrogen, methyl, benzyl or phenyl.

7. The method according to claim 1, wherein Ar is selected from phenyl, substituted phenyl or thienyl, in which the substituent on the substituted phenyl is selected from halo, methoxy or methyl.

8. The method according to claim 1, wherein the time of reaction is 6-15 h.

9. The method according to claim 1, wherein the protective atmosphere is selected from argon, oxygen, air and any combination thereof.

10. The method according to claim 1, wherein the halo is selected from fluoro, chloro or bromo.

* * * * *